(12) United States Patent
Jansen (10) Patent No.: US 9,820,849 B2
(45) Date of Patent: Nov. 21, 2017

(54) INTRAOCULAR LENS, IN PARTICULAR CAPSULAR SAC INTRAOCULAR LENS

(71) Applicant: BIOLNIC UG, Köln (DE)

(72) Inventor: Josef Jansen, Bergisch-Gladbach (DE)

(73) Assignee: Biolnic UG, Cologne (DE)

( * ) Notice: Subject to any disclaimer, the term of this patent is extended or adjusted under 35 U.S.C. 154(b) by 0 days.

(21) Appl. No.: 14/423,039

(22) PCT Filed: Aug. 21, 2013

(86) PCT No.: PCT/DE2013/000472
§ 371 (c)(1),
(2) Date: Feb. 20, 2015

(87) PCT Pub. No.: WO2014/029383
PCT Pub. Date: Feb. 27, 2014

(65) Prior Publication Data
US 2015/0238309 A1     Aug. 27, 2015

(30) Foreign Application Priority Data
Aug. 24, 2012   (DE) ........................ 10 2012 016 893

(51) Int. Cl.
*A61F 2/16* (2006.01)

(52) U.S. Cl.
CPC .......... *A61F 2/1613* (2013.01); *A61F 2/1648* (2013.01); *A61F 2002/1681* (2013.01);
(Continued)

(58) Field of Classification Search
CPC .... A61F 2/1613; A61F 2/1635; A61F 2/1648; A61F 2/1629; A61F 2/1694; A61F 2/1624; A61F 2/16; A61F 2002/1681
See application file for complete search history.

(56) References Cited

U.S. PATENT DOCUMENTS

| 2003/0149480 A1 | 8/2003 | Shadduck |
| 2005/0119740 A1 | 6/2005 | Esch et al. |
| 2006/0047339 A1* | 3/2006 | Brown ................ A61F 2/1602 623/6.13 |

FOREIGN PATENT DOCUMENTS

| EP | 1958592 A1 | 8/2008 |
| WO | WO-2008031231 A1 | 3/2008 |
| WO | WO-2008108525 A1 | 9/2008 |

OTHER PUBLICATIONS

International Search Report (in German with English Translation) for PCT/DE2013/000472, dated May 26, 2014; ISA/EP.

* cited by examiner

*Primary Examiner* — David H Willse
*Assistant Examiner* — Tiffany Shipmon
(74) *Attorney, Agent, or Firm* — Harness, Dickey & Pierce, P.L.C.

(57) ABSTRACT

The present invention relates to an intraocular lens, in particular capsular intraocular lens, with at least an anterior, a posterior optic element, a haptic element connecting both optic elements, wherein a cavity is formed by the optic element, and haptic elements, which are opened by circumferentially arranged openings. The object of the present invention is to provide an intraocular lens that allows a symmetrical deformation of one or more optic elements of the intraocular lens as well as a relative displacement of these optic elements relative to each other on their optic elemental axis, so that a sufficient change in refractive power is obtained. This object is met by an intraocular lens, wherein it is provided that the area of the cavity between the optic elements comprises a filling that is at least partially enclosed by a membrane that
  a) is formed as a bag and completely encloses the filling,
  b) is ring-shaped and is connected to the anterior and posterior optic element or
  c) closes the openings (Continued)

The present invention further relates to an intraocular lens having at least an anterior and a posterior optic element and a haptic element interconnecting both optic elements. According to the invention the haptic element forms an overhang at the transition to the anterior optic element, wherein the anterior surface of the haptic element anterior extends beyond the edge of the anterior optic element or the haptic element forms an overhang at the transition to the posterior optic element, whereby the posterior surface of the haptic element posterior protrudes over the edge of posterior optic element, wherein the anterior or the posterior optic element is preferably embodied as a pinhole.

18 Claims, 9 Drawing Sheets

(52) U.S. Cl.
CPC ............... *A61F 2002/16901* (2015.04); *A61F 2230/0023* (2013.01); *A61F 2250/0003* (2013.01)

INTRAOCULAR LENS, IN PARTICULAR CAPSULAR SAC INTRAOCULAR LENS

CROSS REFERENCE TO RELATED APPLICATIONS

This application is a U.S. National Phase Application under 35 U.S.C. 371 of International Application No. PCT/DE2013/000472 filed on Aug. 21, 2013 and published in German as WO 2014/029383 A1 on Feb. 27, 2014. This application is based on and claims the benefit of priority from German Patent Application No. 10 2012 016 893.4 filed Aug. 24, 2012. The entire disclosures of all of the above applications are incorporated herein by reference.

The present invention relates to an intraocular lens, in particular a capsular intraocular lens, with at least an anterior and a posterior optic element and a haptic element connecting both optic elements, wherein a cavity is formed by the optic element and haptic element, which is opened by circumferentially arranged openings.

The so-called accommodation is the dynamic adaptation of the refractive power of the eye. In the near vision, the natural lens is in its spherical, non-deformed, and unloaded state in which no forces act on them. The ciliary muscle is thereby strained and concentrically contracted and the zonular fibres are relaxed. If the ciliary relaxes (far accommodation), the zonular and the capsular bag through its equator tighten in the radial direction. The capsular bag thereby exerts an axial compressive force on the lens, whereby the latter deforms into a less curved ellipse, so that the farsightedness is enabled. Upon contraction of the ciliary (near accommodation), the lens goes back by its own resilience in its own spherical form, which again is accompanied with an increase in refractive power. The diameter of ciliary and lens as well as the lens thickness vary between near and far vision by about 0.5 mm. The elasticity of the lens deteriorates as one gets older and eventually leads to presbyopia. The correction is usually done with a pair of glasses.

A particularly serious occurrence as age slowly progresses is cataract, which is opacification of eye lens. The consequences of such a cataract are increased glare sensitivity of the eye and the faded colour perception. Advanced cataract can only be treated surgically. For this purpose, the lens is first destroyed by ultrasound, vacuum cleaning and then an artificial, usually rolled, intraocular lens is injected through a small incision in the cornea into the open capsular bag.

The known state of the art intraocular lenses are mono-focal, thus they have only one focal point. Using the so-called haptic elements, the optic elements of intraocular lenses are usually centred in the capsular bag. Aspherical lenses improve contrast and night vision by avoiding scattered light, while intraocular lenses with special (UV) filters protect the retina. Materials with a high refractive index are also advantageous to be able to produce thinner lenses or intraocular lenses for smaller incisions with the same dioptric power. Minor cuts must not be closed with a seam. In addition, the likelihood of postoperative astigmatism is significantly reduced.

In addition, according to the state of the art bifocal or multifocal lenses are known. The disadvantage of the multifocal lies in the much poorer sensitivity to both contrast and increased glare.

The most common complication with the use of intraocular lenses is the postoperative after-cataract. This arises in large part by proliferation of residual or regenerated lens epithelial cells, remaining in the capsular bag after extra capsular cataract extraction. The after-cataract requires a laser treatment that can be associated with potential complications. A crease-free relaxation of the posterior capsular is considered as a possible effective after-cataract prophylaxis.

Despite numerous attempts, it has not yet been managed to restore accommodation of the eye with sufficient refractive power change for a longer period.

Most concepts for restoration of accommodation provide the implantation of an intraocular lens in the capsular bag ("capsular intraocular lenses").

Here, two basic approaches can be distinguished, namely intraocular lenses according to the so-called "optic element shift principle" and the lens capsular refilling ("lens refilling") with liquid or viscous materials. However, the lens capsular refilling has not been successful due to various problems.

In the optic element-shift principle, one or two optic elements are displaced along the optic elemental axis of the intraocular lenses. However, a sole displacement of the optic element on the optic elemental axis does not reach a satisfactory accommodative power, since the displacement is limited.

In addition, intraocular lenses that are not implanted in the capsular bag and with haptic elements in direct contact with the ciliary (so-called ciliary intraocular lenses) also belong to the state of the art. For implantation, the capsular bag is initially removed or is at least located partially posterior of the intraocular lens after implantation. Such intraocular lenses can be used in the sulcus of the posterior chamber or the ciliary muscle or be attached to the sclera.

The main advantage of a ciliary intraocular lens compared with a capsular intraocular lens is in a significantly higher power transmission potential, caused by the direct connection to the ciliary that can lead to a significantly higher accommodative power of the intraocular lens.

In the optic element shift principle, non-capsular bag filling and capsular bag filling intraocular lenses can be used. The non-capsular bag-filling intraocular lenses cannot deform the optic element a priori.

In the capsular bag-filling intraocular lenses, a capsular bag-like envelope, namely the haptic elements and the lenses arranged at the poles of the envelope almost entirely fill the capsular bag. Here, embodiments with one, two, or three lenses are known, but the materials and design versions of these intraocular lenses are generally too rigid for the lenses to deform sufficiently due to the axial compressive forces of the capsular bag induced by the zonular. In some known intraocular lenses, the haptic elements in the equatorial section are too stiff, so that a change in diameter of the haptic element is not possible. Such intraocular lenses are described, for example, in EP 0766540, U.S. Pat. No. 6,551,354B1 and US 2004/0111153A1. From US 2007/0260310A1 and U.S. Pat. No. 6,488,708B2, for example, intraocular lenses are known, which allow only axial displacements of the lenses to each other, due to the shape of the haptic elements and the lens.

The object of the present invention is to provide an intraocular lens that allows a symmetrical deformation of one or more optic elements of the intraocular lens as well as a relative displacement of these optic elements relative to each other on their optic elemental axis, so that a sufficient change in refractive power is obtained.

This object is met by the intraocular lens according to claim 1, wherein it is provided that the area of the cavity between the optic elements comprises a filling that is at least partially enclosed by a membrane that a) is formed as a bag and completely encloses the filling,
b) is ring-shaped and is connected to the anterior and posterior optic element or
c) closes the openings.

Accordingly, the filling can be isolated within the intraocular lens, which is particularly convenient for a liquid filling to integrate the filling inside the very thin bag. Alternatively, the filling can be separated radially outwardly by a membrane from the rest of the intraocular lens and/or of the aqueous chamber. The membrane spans in this case preferably between the respective bases of the anterior to the posterior haptic element, that is, between the edges of the lenses. The membrane may extend radially outwardly so as to compensate for a change in volume between far and near vision. Another possibility for sealing the cavity is to close the haptic element openings with a thin membrane. The membrane or bag that closes the cavity radially outwards is substantially thinner in comparison with the shell of an intraocular lens should lie in the order of about one-tenth of the thickness of the shell. The thickness of such a membrane is preferably between 5 µm and 50 µm.

Advantageous embodiments of the present invention are described below and in the subordinate claims.

In a first preferred embodiment, it is provided that the area of the cavity, which is bounded by the haptic element and/or the openings, is partially or completely occupied by the filling. Accordingly, the filling can preferably fully lie against the two outer lenses. The inner surfaces of the optic elements in this case may be of any shape, particularly when lenses, filling, and where applicable, the bag have the same refractive index. The filling can completely fill the interior of the intraocular lens, or be limited to the area of the optic element. If the filling extends beyond the optic elemental area in the haptic element and if the latter is not liquid or gaseous, then the filling in the section of the haptic element as the haptic element itself is preferably provided with openings, in particular when the filling is connected with the haptic element. The design of gel-like soft filling and harder shell, given appropriate thickness distribution of the shell and suitable modulus of elasticity, allows the controlled deformation of the intraocular lenses to achieve adequate optic elemental imaging in the near and far state, up to the border area of optic elements. Stray light problems can thus be prevented or reduced significantly even when the iris is wide open. Such a change in shape of the intraocular lens cannot be achieved if the filling would be surrounded by only a very thin or pliable membrane or shell.

The filling is in liquid, gel, or gaseous form according to a preferred embodiment of the invention and comprises nano-particles according to a particularly preferred embodiment. The filling serves to increase the accommodative power, for which the filling of the intraocular lens preferably has a higher refractive index than that of aqueous humour. In addition, the medium or material of the filling is relatively softer and/or more elastic than the shell.

The filling or the bag with the filling is preferably connected completely or also only partly with one or simultaneously with two optic elemental surfaces or it may lie loosely in the interior of the intraocular lens. Thus, also interstices can occur between external optic elements and the filling that fill with aqueous humour as the case may be. In addition, the filling may also be divided so that a gap or interstice is formed in the centre in each case and the divided fillings are connected to the external optic elements. The bag can be inserted through the openings into the interior of the intraocular lens.

In the cavity of the intraocular lens or in the filling also one or possibly several other optic elements can be integrated.

According to an alternative embodiment, the filling consists of a hydrophilic material (hydro gel) such that the intraocular lens in the dry state and with a smaller volume can be easily implanted. After the implantation into the eye, the filling absorbs water from the aqueous humour and acquires the size and shape of the intended optic elemental function of the intraocular lens. For this design, the possibly existing, previously described, separating membrane or the intraocular lens itself should be water-permeable. For this purpose, the membrane, for example, could be perforated. Alternatively or additionally, only the haptic element could be perforated or permeable to water by diffusion, so that the aqueous humour can penetrate into the cavity.

It has already been explained, that the intraocular lens comprises at least two lenses, wherein preferably at least one of them changes its shape during accommodation. The natural shape or production condition is preferably a round shape for near vision. Force is transmitted to the intraocular lens mainly due to axial forces via the capsular bag to the haptic element and thus on the lens. The intraocular lens is also suitable as a continuously focusable lens for technical low-cost applications.

According to a preferred embodiment of the invention, the intraocular lens consists of two substantially (from anterior to posterior) convex-concave or concave-convex-shaped, half-shells with integrated optic element at the poles, which are connected to each other via the haptic element. Preferably, the haptic element has an anterior and a posterior haptic segment that are connected to each other at the equator. Dual curved shells can be deformed into less curved or flat shells only with relatively large forces. Therefore, the haptic element part of the intraocular lens from the equator to the lens has radially aligned apertures, whereby the deformation forces of the shells needed for a change in refractive power are significantly reduced. In other words, the anterior and posterior haptic segments have a plurality of haptic elements that are substantially configured in a triangular shape, wherein the bases of the triangular haptic elements transform into the respective optic elements.

Preferably, the bases of two adjacent triangular haptic segments abut one another, so that the intraocular lens forms star-shaped shells in a plan view. Furthermore, the tips of two opposite haptic elements are connected to each other. An intraocular lens thus formed may expand due to the small connection surface in the equatorial area of the two shells under far accommodation with minimum forces, i.e. increase their diameter, while reducing the thickness of the intraocular lens. The cross-sectional area of the triangular haptic elements preferably increasing from the equator to the poles can distribute and transmit the axially opposing forces, required for change in the curvature of the optic element, very uniformly around the circumference of the optic elemental element. The refractive change of the optic element is rotationally symmetrical and the image without distortion.

According to another preferred embodiment of the present invention, it is provided that the leg of the triangular haptic elements is straight, convex, or concave in a plan view. As a result, the flexibility of the capsular intraocular lens is advantageously increased. The bases of the triangular haptic elements may have even small distances from one another on the periphery of the optic element.

The intraocular lens consisting of haptic and optic element is designed so that it almost completely fills the capsular bag and stretches out wrinkle free. The capsular bag is in direct contact with the haptic element and particularly the posterior optic element, so that the risk of cataract formation is reduced. In the equatorial section, however, the haptic element of the intraocular lens does not necessarily fill the capsular bag completely, but this is desirable, since otherwise centring of the lens in the capsular bag may be affected.

The diameter of the optic element is preferably designed such that it is slightly larger than the opening of the anterior capsular bag. The opened capsular bag is required for the injection of the intraocular lens into the capsular bag. The opening of the anterior capsular bag is usually about 5 mm in diameter. Owing to this the axial pressure and/or counter pressure of the anterior capsular on the intraocular lens is missing in this opening in the central section of the optic element. Only axial compressive forces acting directly on the intraocular lens in the area where anterior and posterior capsular bags are congruent are applied, i.e. depending on the size of the capsular bag opening, mainly outside the optic element and thus in the area of haptic elements.

According to a particularly preferred embodiment of the present invention, along the circumference of an optic element at least three, preferably six and more preferably at least eight triangular haptic elements are disposed. The cumulative width of the tips of the haptic elements, which results from the sum of the widths of all peaks is less than 40%, preferably less than 30%, and more preferably less than 25% of the equatorial circumference. It has already been shown that the bases of the triangular-shaped haptic elements are preferably connected to each other, although also cumulative distances of 5%, 10%, or 20% of the circumference corresponding to the radius of the bases are tolerable in order not to keep non-rotationally symmetrical distortion of the optic element low.

Due to the above-described design of the haptic elements, the intraocular lens may very well be compressed during far accommodation. However, due to the anterior opening of the capsular bag only very small deformation forces act on the optic element, which may flatten sufficiently in their central optic areas in order to achieve the required accommodative power. According to a further particularly preferred embodiment of the present invention, therefore the anterior haptic segment forms at the transition to the optic element an overhang, wherein the anterior surface of the anterior haptic segment projects anterior beyond the edge of the anterior optic element. Further, it is preferably provided that the posterior surface of the anterior haptic segment projects beyond the posterior surface of the anterior optic element. Further, the anterior optic element is particularly preferably a diverging lens, that is, the anterior optic element is in the edge area at least as thick or thicker than at the central optic element axis and preferably has a convex outer surface. By this design the anterior part of the haptic element directed towards the equator in case of far accommodation is deformed, anterior, so that a moment comes that flattens the anterior optic element and in appropriately designed wall thickness and elastic modulus deforms up to inside out turn, that is, an anterior convex surface of the anterior optic element can be transformed into a concave surface. In this case, the centre of the anterior optic element can be shifted to posterior at least by approximately half the thickness of the intraocular lens. With this preferred design, the greatest possible deformation and posterior displacement of the anterior optic element is achieved.

Basically, the overhang described above can also be much more pronounced, to the extent that the posterior surface of the anterior haptic element extends towards anterior over the edge of the anterior optic element, wherein, the haptic segment may be made somewhat stiffer here than the optic element.

The haptic element should preferably be connected flush with the optic element so that the haptic element transforms into the optic element without thickness steps. However, even small differences in thickness can be formed, provided that the necessary ductility of the optic element is not affected unduly. It has been found that with thickness differences of 80% to 90%, the operation is still substantially maintained.

Comparatively larger thickness differences can be tolerated on the anterior optic element in the presence of the previously described "overhang" of haptic elements. Since in the embodiment of the intraocular lens with "overhang" the posterior optic element can be comparatively deformed towards the anterior optic element, little or minor posterior optic element can be equipped with different dioptre values, or convex-convex elements to compensate an existing patient-specific visual defects such as short sightedness or long sightedness. Therefore, greater thickness differences may be tolerated also posterior in such an embodiment.

Analogously to the embodiment of the overhang between the anterior haptic element and the anterior optic element is provided according to an alternative embodiment that projects beyond the anterior surface of the posterior haptic segments the anterior surface of the anterior posterior optic element. The posterior surface of the posterior haptic segments may further protrude the posterior surface of the posterior optic element, posterior.

According to an alternative embodiment besides the described star-like shape, the intraocular lens with high flexibility at the equator and flush transition from haptic elements to optic element can also be achieved by two fully flat design shells, firstly by radial cuts from the equator to the edge of the optic element, and secondly by circumferential sections slotted on the equator. The slots on the equator go so far until the web-like triangular vertices remain as connection of the two half-shells. In a side view on the equatorial section, cross-shaped slots are then obtained. Through this configuration of the slots, the haptic elements are also axially elastic so that the transmission of force from the haptic element to the optic element is similarly uniform as is realised in the star-shaped intraocular lenses.

The outer diameter of the intraocular lens in the production and near range is 7 mm to 11 mm. In contrast, the diameter of the optic element of the intraocular lens is 3.5 mm to 7.5 mm. Finally, the thickness of the intraocular lens at the poles is preferably 2.5 mm to 6 mm. The wall thickness of the anterior optic element as a function of its modulus of elasticity is between 0.1 mm and 1 mm, particularly preferable between 0.25 mm and 0.75 mm. The wall thickness of the posterior optic element lies in a larger range, since it can also assume a convex-convex shape; particularly this optic element can be thicker than 2 mm in the central optical range.

In the case of use of the intraocular lens as a ciliary intraocular lens, the above-indicated dimensions may be somewhat larger.

For the implantation procedure, the correct size selection of the intraocular lens is taken into account. To relax the capsular bag possibly wrinkle-free, a capsular intraocular lens can be selected with a diameter that is larger than the diameter of the capsular bag, or an intraocular lens is selected with a thickness that is greater than the thickness of the explanted lens. Preferably, an implantation method is proposed in which a thicker implant is inserted, so that the capsular bag is relaxed wrinkle-free and wherein the diameter of the intraocular lens is equal to or preferably smaller than the diameter of the capsular bag in near range (of non-operated eye). This enables the greatest possible change in the equatorial diameter of the capsular bag at far accommodation, i.e. for relaxed ciliary and tensioned ciliary zonular. The decisive factor in this size range, with focus on the thickness is that the zonular fibres are possibly streamlined in the near range of the capsular intraocular lens, i.e. at full contraction of the ciliary or almost streamlined, so that upon relaxation of the ciliary a maximum possible expansion of the capsular bag is achieved. In this respect, the maximum possible tension of the zonular is exerted on the capsular bag. Upon using a larger diameter of the intraocular lens, however, the tension and/or the pull of the zonular on the capsular bag is reduced and in extreme cases the zonular are relaxed even with completely relaxed ciliary, i.e. the ciliary is relaxed with maximum diameter.

It should be mentioned that it would be possible in principle after implantation of the intraocular lens to close the capsular bag again to increase the accommodative capacity of the overall device.

The implantation method of the capsular intraocular lens is supplemented by another possibility for the liquid exchange during accommodation or for the penetration of liquid into the cavity of the intraocular lens. These small openings (holes) are introduced into the capsular bag along the equatorial circumference between the zonular fibres. Through this design of the openings on the equatorial circumference, the mechanics of the zonular capsular bag apparatus is not affected or only minimally. This process variant is advantageous in particular because the intraocular lens can be filled, after it has been inserted into the capsular bag and fluid or aqueous humour flows or diffuses out of the interior of the eye through the openings of the capsular bag, the haptic openings, and then the membrane into the cavity of the intraocular lens.

The intraocular lens with a filling can be implanted in another way in a smaller state when the cavity is filled only after the implantation. For this purpose, preferably a reservoir detachably connected with the cavity is provided, so that the filling is fed from the reservoir into the cavity. The intraocular lens is implanted in a flattened state.

According to a preferred embodiment, the reservoir is tube-shaped and is preferably connected with the cavity via a micro-valve or via a cannula or hollow needle. Here, the tubular reservoir could be turned inside out over the end of the valve as a water hose via a shut-off valve. Alternatively, the reservoir can also be connected via a hose with the hollow space that can be separated by fusion. On the other hand, the tubular reservoir could be connected with the cavity by means of a cannula, which forms the open end of the reservoir. After removal of the cannula, the punctured spot closes again. In addition, the punctured spot in the form of a rubber plug or nipple ("rubber closure to be pierced") could be reinforced. Advantageous for tight sealing of the puncture is that the very soft polymers needed for such an intraocular lens are usually very sticky. Furthermore, the valve between the cannula and reservoir could be optionally connected. The connection or interface between the cavity and the reservoir is preferably disposed on the membrane, or on the haptic element or outside the optic element zone of the optic element. If necessary, the cavity is additionally connected to a vent hose in order to avoid any blistering effect. The vent tube can be analogously connected to the reservoir with the cavity. The advantages of the detachable reservoir for filling the cavity are that a pre-filled and pre-assembled intraocular lens with a defined capacity can be delivered to the ophthalmologist. In overall, incorrect manual processes such as incorrect filling quantities and/or contamination are reduced.

In addition to the detachable reservoir, the intraocular lens could have another or possibly also several other smaller reservoirs for volume exchange between near and far accommodation. These reservoirs may be preferably arranged in a ring form in the interstice outside the membrane and within the haptic element.

The cavity could also be filled via a micro-metering pump. These operations can occur outside of the eye. The remaining tube rest after sealing the tube, which are connected to the cavity of the intraocular lens, can be moved into the interior of the eye and possibly pulled into the remaining cavity between haptic elements and membrane. The filling may also be injected via syringe. The filling process could be so used to adjust the refractive dioptre number.

Another possibility to implant the intraocular lens with the smallest possible volume into the eye is the introduction of the bag or the filling after the implantation via the haptic openings into the interior of the intraocular lens.

The present invention further relates to an intraocular lens having at least an anterior and a posterior optic element and an optic element interconnecting both haptic elements. Such an intraocular lens need not have a filling, so that to increase the accommodation power according to the invention a) the haptic element at the transition to the anterior optic element forms an overhang, wherein the anterior surface of the haptic element protrudes beyond the edge of the anterior optic element, or b) the haptic element at the transition to the posterior optic element forms an overhang, wherein the posterior surface of the haptic element protrudes beyond the edge of the posterior optic element, wherein the anterior or posterior optic element is preferably formed as a pinhole.

Preferably, the thickness of the anterior haptic element is formed in the transverse section to the optic axis, at least as thick as the thickness on the edge of the anterior optic element. Alternatively, the thickness of the posterior haptic element, in the transverse section to the optic axis, is at least as thick as the thickness on the edge of the posterior optic element. In both cases it is preferably provided that the posterior surface of the anterior haptic element protrudes beyond the posterior surface of the anterior optic element, or that the anterior surface of the posterior haptic element extends beyond the anterior surface of the posterior optic element.

The intraocular lens if necessary without filling and possibly with a pinhole as anterior or posterior optic element is formed analogously to the intraocular lens with a filling. The optic elements are thus interconnected via a haptic element, wherein the haptic elements comprise two haptic segments. The haptic segments may also consist of plurality triangular-shaped haptic elements, which merge at their bases in the respective optic element and which are connected together at the tips. Furthermore, reference is made to the above statements.

It should be noted that other haptic forms could be used. Further, the intraocular lens can be used without filling also according to the optic element shift principle, in which the optic element section of the half-shell is formed with overhang in the central area as biconvex optic element and other optic elements as described above or below, or as a pinhole.

To simplify the assembly of two intraocular lens half-shells, it is proposed to mould the half-shells in each case as a radial annular portion having a contact surface, wherein the half-shells are connected to each other via these contact surfaces. In other words, the half-shells have a kind of hat brim along the equator, so that when joining a larger contact area is provided. The annular portions of the two half-shells are preferably designed such that, for example, annular tongue and groove elements interlock during assembly and centre themselves to each other, so they have an additional positive lock. It is also intended for further reinforcement that in the radial section a thin ring of metal or plastic be incorporated. The thin rings are designed such that they engage when joined can and thereby also an angular alignment are achieved. After joining the intraocular lens half shells the radial portion and optionally the openings are separated. However, it is also envisaged that, where appropriate, a ring-shaped rest of the annular portion is not removed along the equator of the half-shells, so that the tips of the haptic elements are connected to each other via thin annular elements. In thin connections the flexibility and thus the contraction and the accommodative capability of the intraocular lens is only slightly restricted. According to an alternative embodiment of the radial pieces they can also have openings, so that almost only the tips of the haptic elements are radially extended to the outside. Also in this embodiment, the stiffening rings may be inserted.

Preferably, the intraocular lens is made of two half shells, which are joined by means of gluing or welding and thus connected to one another by adhesive force.

However, the intraocular lenses can also be composed of two half-shells thus be in two pieces, and be connected positively or frictionally. According to a further preferred embodiment of the intraocular lens it is therefore intended that the tips of the haptic elements be surrounded by a thin strip or a membrane. Such a band does not limit the contractility of the haptic element. The inside of the band between haptic peaks is preferably coated as well as the side surfaces of the haptic elements with anti-proliferative substances, so that no cells can grow into the apertures.

The haptic elements are distributed preferably evenly and uniformly over the periphery of the optic element and the bases of the haptic elements lie together. The bases of the openings between the haptic elements do not extend to the optic element, whereby the depth of the openings may be smaller than the radial length of the haptic elements. According to a further embodiment of the present invention, the widths of the openings vary at the bases of the haptic elements and/or the widths of the bases of the haptic elements themselves in order to deform the optic element unevenly and thus compensate image defects, such as astigmatism of the patient. For this compensation, but also independently thereof, it is provided that the individual haptic elements of an intraocular lens have different shapes or different modulus of elasticity from the optic element. In addition, the configuration of the haptic elements of the anterior opposite the posterior intraocular lens half-shells differ with regard to their shape, width and height from each other in order to achieve an optimum elasticity and deformability adjustment with respect to the accommodation.

The edges of the haptic elements are preferably square or sharp. However, also rounded corner edges may be provided, in particular at the inner edges of the haptic segments towards the cavity of the intraocular lens. Therefore, the haptic elements for example can be circular or elliptical in cross-section in addition to the preferred rectangular shape. The surface of the haptic elements is formed according to a preferred embodiment, structured, or provided with a biologically active coating, whereby the risk of cataract or bacterial adhesion is reduced or avoided. As coating agents, preferably polysaccharide coatings, heparin, hyaluronate or other active ingredients are provided.

To avoid stray light and glare, which happens at night in particular, the haptic elements are preferably formed diffuse, coloured, opaque, doped or surface-structured.

Furthermore, the haptic elements can be provided with a label of identification, a product code, or serial number.

The shapes of the anterior and posterior lenses or other optic elements, if necessary, can have bi-convex, plano-convex, plane-parallel, meniscus, concave-convex, or other lens shapes. The two optic elements can also have different diameters and/or different refractive indexes. When the anterior or posterior optic elements have identical refractive indices, such as the filling, the inner surfaces of the posterior or anterior optic element can be of any shape and differ from classical optic element forms.

The optic element or optic elements of the intraocular lens of this invention, particularly the outer surfaces thereof are preferably aspherical moulds, that is, they are different from the spherical shape. The radii of curvature of the optic elements increase from the central optic element axis to the edge of the optic element preferably by more than 20% and particularly preferably by more than 50%. In certain designs the increase in radius may also be 100% or more than 300%.

In a modified embodiment of the intraocular lens it is designed in a flat shape and can therefore be used as ciliary intraocular lens. For the accommodation, the ciliary muscle presses on the equator or the haptic tips of the intraocular lens and deforms it into the desired round shape.

The shown design of the intraocular lens can be used as purely optic shift intraocular lenses in which the lenses are only moved on their axis and not deformed. In addition, the intraocular lens could be implanted both in the capsular bag, or indirectly coupled to the ciliary.

Different materials come into question as suitable materials for the intraocular lens. According to an embodiment of the present invention an intraocular lens is provided, wherein the intraocular lens consists of a silicone, in particular a thermo-plastically processable silicone. Particularly polymers from the group of organopolysiloxane/polyurea/polyurethane block polymers are useful as thermoplastic silicone types. Preferably, it is provided that the silicone used is cross-linked after joining. However, also thermoplastic polymers and cross-linked thermoplastic polymers or elastomers can be used which have a high optic element transparency and, preferably, a high refractive index. Such polymers and copolymers or mixtures thereof, if necessary, may include the group of the various polyacrylates and polymethacrylates (as well as "PHEMA", "PHPMA", etc.), poly-n-butyl methacrylate) (PBMA), polyvinyl (polystyrene, polyvinyl acetate, poly-N-vinylpyrrolidones "PNVP"), ethylene vinyl acetates, the group of polysiloxanes (PDMS), polyphosphazenes, polyurethanes, polyureaurethanes and their copolymers including $NH_2$- or OH-terminated polyisobutylene polyurethanes, other hydrogels including polyethylene glycol-based hydrogels, polysulfones; styrene-ethylene-butylene-styrene-based thermoplastic elastomers (SEBS), or hydrogenated styrene block copolymers, polystyrene-block-isobutylene-block-styrene (SIBS), include polypropylene. Among these polymers, preferably polystyrene-block-isobutylene-block-styrene (SIBS) or polyurethanes based on $NH_2$- or OH-terminated polyisobutylene are used. The implant material must also be biocompatible and bio-stable. The polymers are thus surface-modified to improve their biocompatibility, which is preferably carried out by hydrophilisation. The polymers may also be water permeable.

The filling in particular can be made of a super-elastic polymer or liquid. In addition to the aforementioned polymers, in particular other hydrophilic polymers are suitable, such as polyvinylpyrrolidone, polyvinyl alcohol or hyaluronic acid. These can be mixed with water, particularly suitable for this purpose is also linked polyvinylpolypyrrolidone (PVPP). The liquid can be water or an aqueous dispersion or colloid-dispersed solution in which nanoparticles preferably made of polymers are added to increase the refractive index. In particular, the filling may also be made of halogenated hydrocarbons, in which polymethyl methacrylate particles are added. The nano-particles may also have functionally adapted surface or be coated with noble metal colloids (for example, gold). Furthermore gold sole is useful as a filling liquid.

To increase the refractive index of the polymers or of the filling medium, other nano-particles, such as titanium dioxide may be added. Preferably, the polymer nano gold can be added or bonded to it chemically (covalently). If gold is added, the intraocular lens obtains anti-bacterial properties. In addition, the polymer or the filling can thus filter blue light, which protects the retina as a UV barrier.

The modulus of elasticity of the polymer according to an advantageous embodiment is less than 1 N/mm$^2$.

The shell or half-shells of the intraocular lens are preferably made of a polymer having an elastic modulus less than 0.1 N/mm$^2$, more preferably less than 0.05 N/mm and preferably greater than 0.001 N/mm$^2$. The filling of the capsular intraocular lens is, as already stated above, preferably liquid or gaseous, if a polymer or gel is involved, the modulus of elasticity is less than 0.001 N/mm$^2$, and preferably less 0.0001 N/mm$^2$. In one embodiment of the intraocular lens as ciliary intraocular lens, the modulus of elasticity of the shell can be higher than the above-indicated values for the shell.

The intraocular lens according to the present invention can be used also for other technical purposes, for example as a continuously focusable optic element for 3D endoscopes equipped with an integrated camera, PC monitors for high-quality video conferencing or autofocus lenses in the low-cost sector. The accommodation here could be controlled over radially acting actuators, such as with an air-filled or fluid-filled hose.

Specific embodiments of the present invention are explained as follows and with reference to the Figures. Shown in the drawings:

FIGS. 2a to 3c show various embodiments of intraocular lenses, FIG. 4a, b: Intraocular lenses with an annular surface portion, FIG. 5a, b: Intraocular lenses with a reservoir and FIG. 6: a ciliary intraocular lens FIGS. 1a and b each show a sectional view of an eye 1 with the cornea 2 and the sclera 3 and a capsular intraocular lens 11 disposed within the capsular bag 12. The capsular bag 12 is connected via the zonular fibres 13 connected to the annular ciliary muscle 14. In the near vision (FIG. 1a) the intraocular lens 11 is in its spherical and non-deformed state with no radial forces acting on it. In this case, the ciliary muscle is tense and 14 concentrically narrowed so that the zonular fibres 13 are relaxed. For distance vision (FIG. 1b), the ciliary muscle 14 relaxes, so that the zonular fibres 13 tighten and the capsular bag 12 in the radial direction become taut. In this case the capsular bag 12 exerts an axial force on the intraocular lens 11, whereby this reduces its curvature and thus the refractive power decreases.

Concrete embodiments of intraocular lenses according to the invention are shown in FIGS. 2a to 3c. The intraocular lenses 11 shown there consist of two opposing shell-shaped lenses 21, 22 and the connecting haptic elements 23. As already apparent from FIGS. 2a to d, 2f, and g and in particular from the cross-sectional views (FIG. 2c near vision, FIG. 2d distant vision) the haptic elements 23 transform preferably flush into the optic element 21, 22.

According to a concrete embodiment of the present invention, the haptic elements 23 consist of haptic segments, which in turn comprise a plurality of triangular-shaped haptic elements 24, wherein the bases of the haptic elements 24 are connected to the optic element 21, 22. The tips 25 of two haptic elements 24 disposed opposite the bases are connected by webs 26.

Furthermore, according to the illustrated embodiment, eight haptic elements 24 are provided, whereby the bases of two adjacent haptic elements 23 are in contact with each other (arrow 27).

Figure 1A:
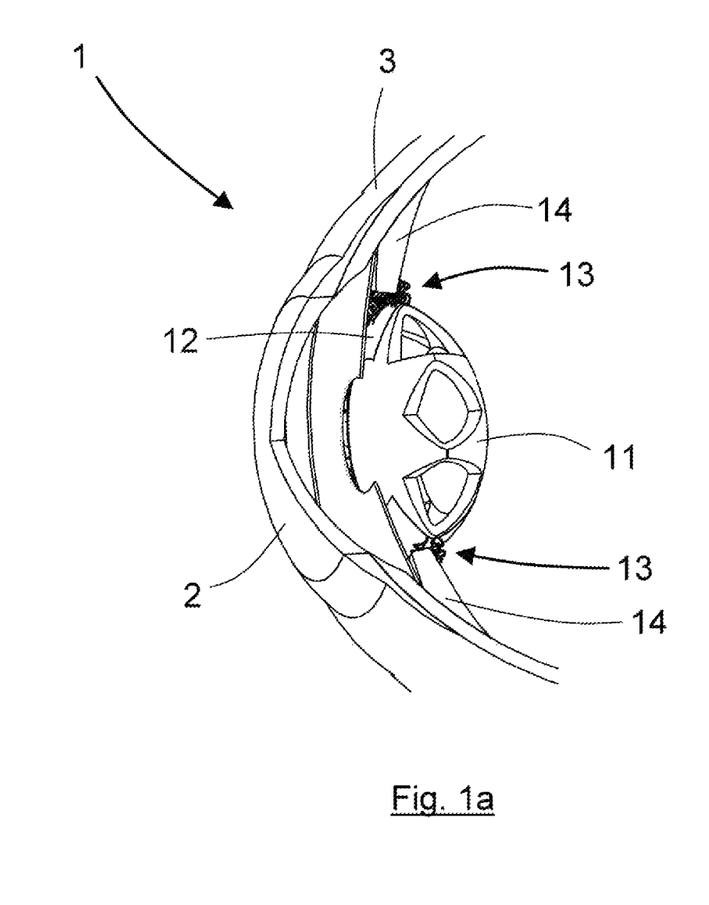
FIG. 1a, b. depending on a schematic representation of an implanted capsular intraocular lens.
Figure 1B:
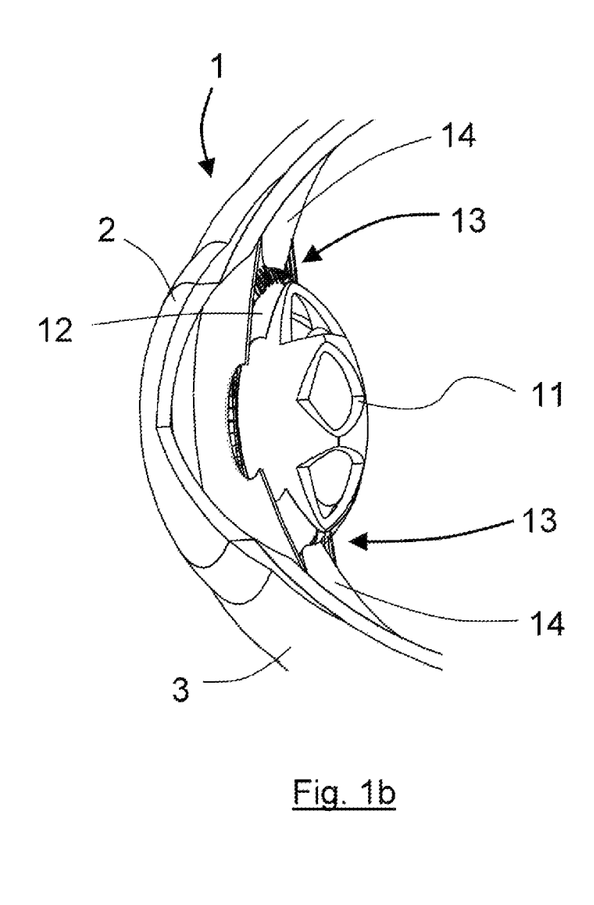
Figure 2A:
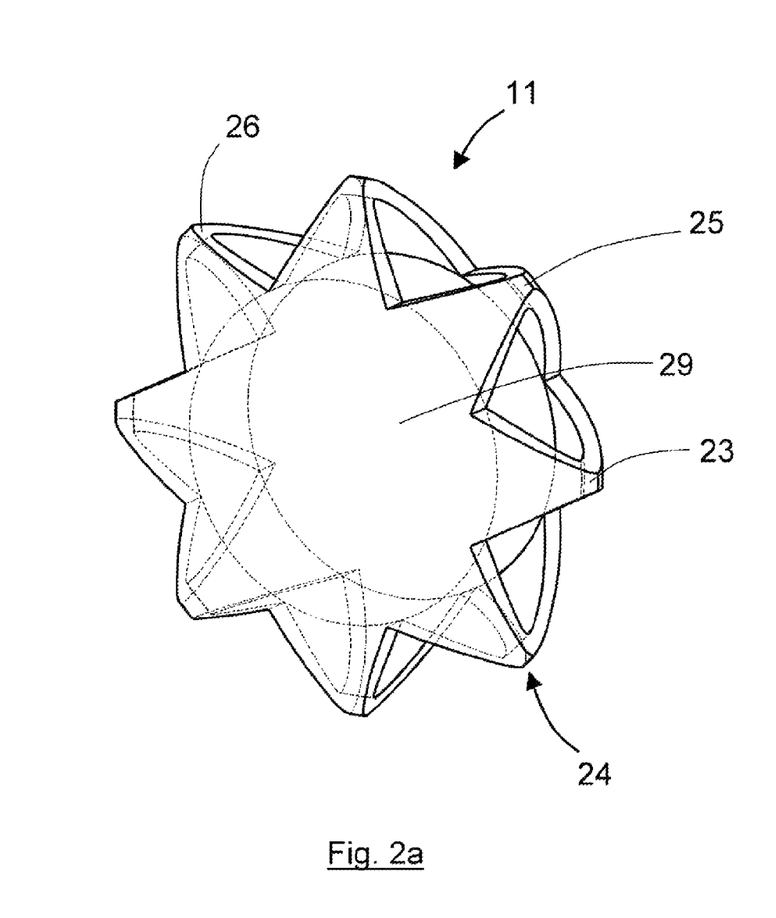
Figure 2B:
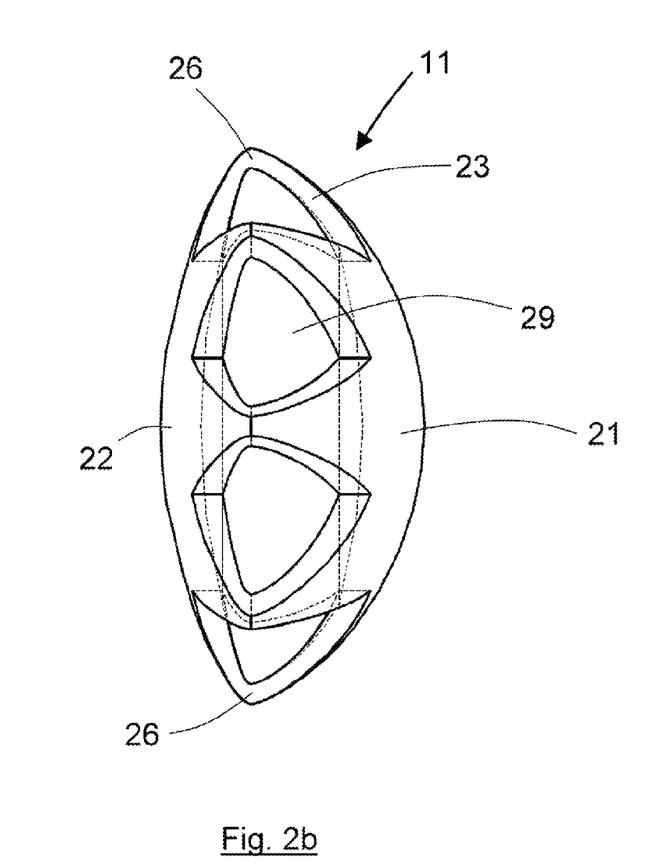
Figures 2C, 2D:
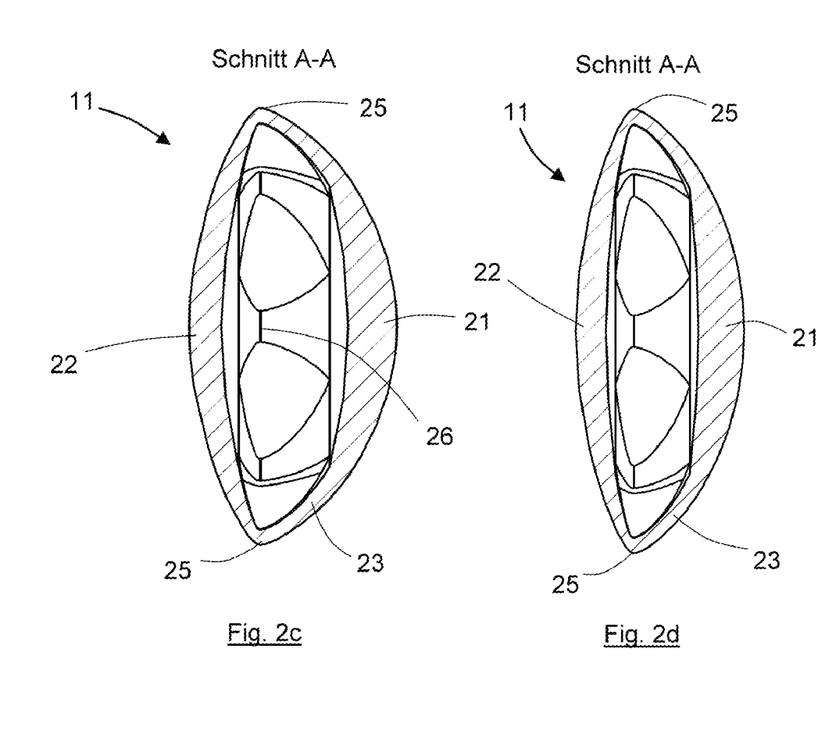
Figure 2E:
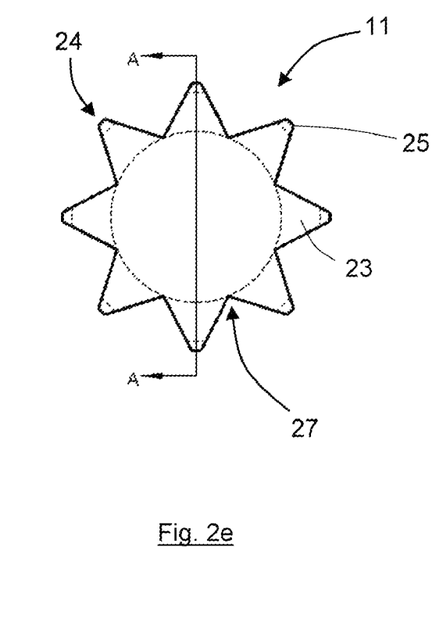
Figure 2F:
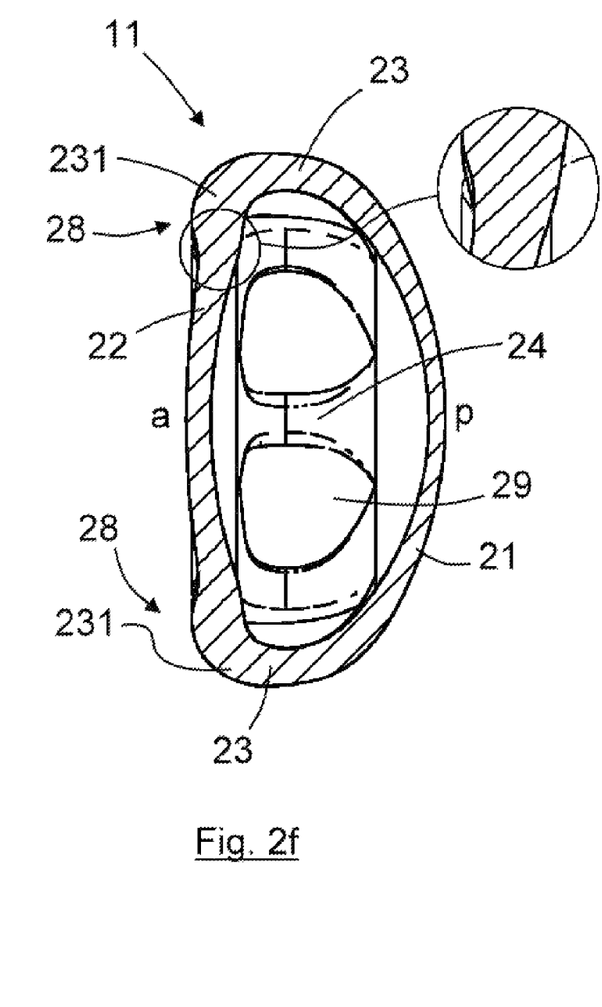
Figure 2G:
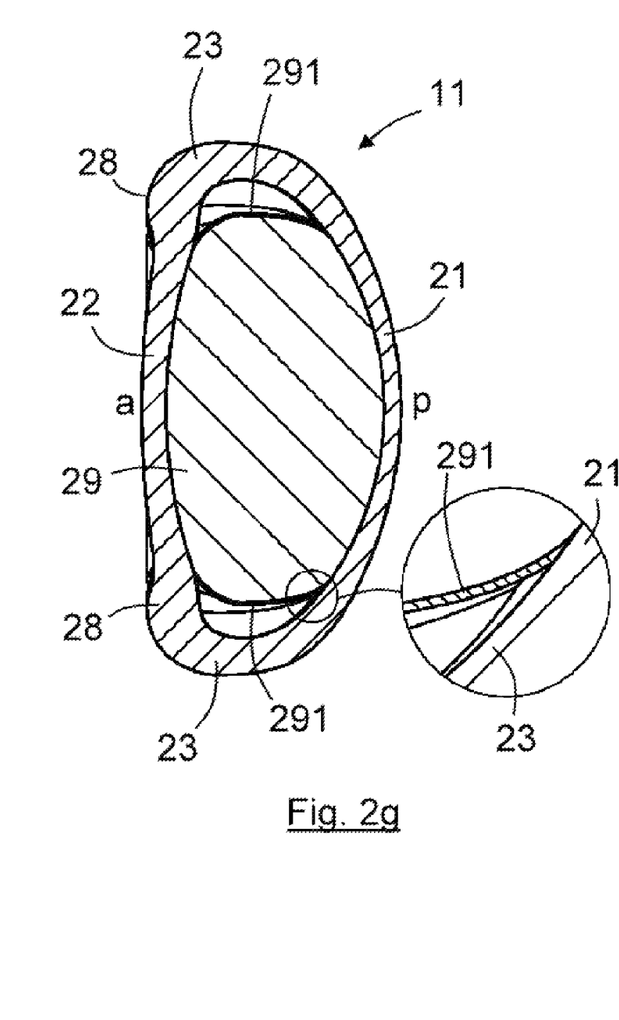

FIGS. 2f and 2g show cross-sections of an intraocular lens with an overhang of the haptic element 23 to the optic element 22 in near range, wherein the direction information is marked anterior with "a" and posterior with "p". It is clearly shown that the anterior haptic segment 231 at the transition to the optic element 22 forms an over-hang 28, in which the anterior surface of the anterior haptic segment 231 protrudes, anterior over the edge of the anterior optic element 22. In addition, the posterior surface of the anterior haptic segment 231 protrudes over the posterior surface of the anterior optic element 22. In the illustrated embodiment, the anterior optic element 22 is formed as a diverging lens.

Figure 2H:
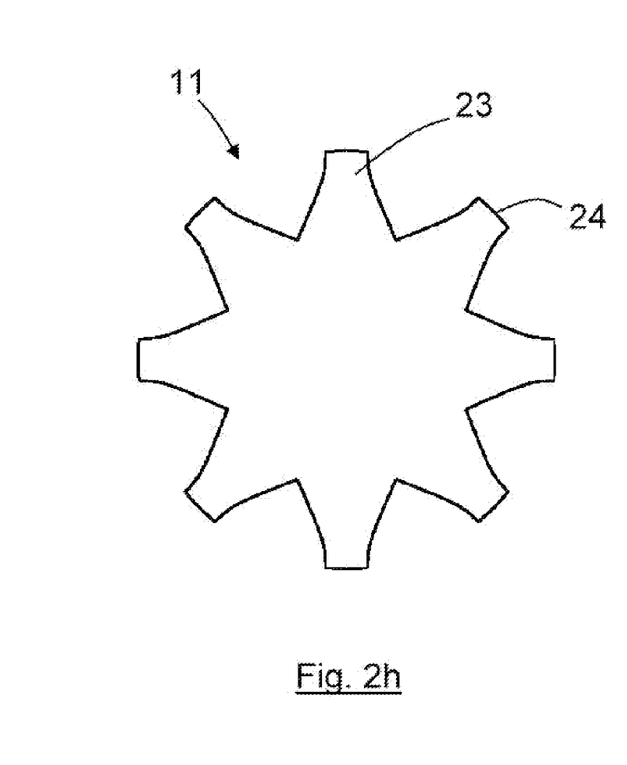
Figure 2I:
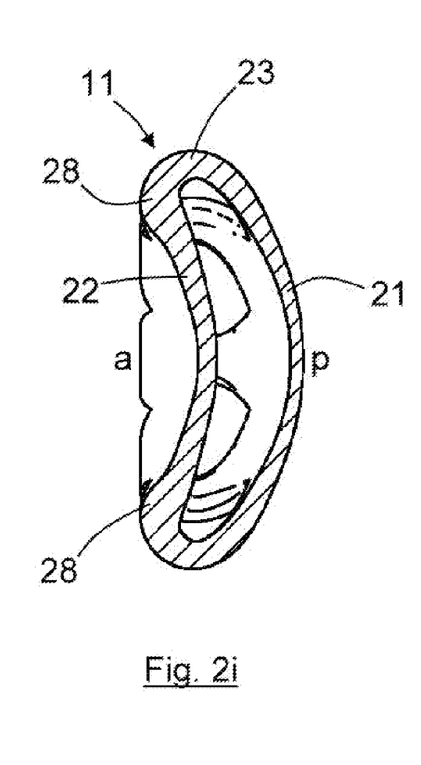
Figure 2J:
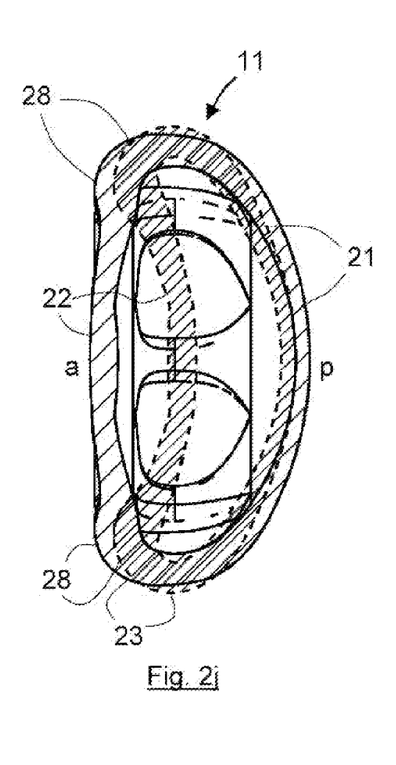

By this design in case of far accommodation, the anterior part of the haptic element 23 directed towards the equator is deformed anterior, so that a moment occurs that flattens the anterior optic element 22 and in appropriately designed wall thickness and elastic modulus deforms up to inside-out turn, as shown in FIG. 2i, wherein the lens is depicted in the far range. Hereby an anterior convex surface of the anterior optic element is transformed into a concave surface. In this case, the centre of the anterior optic element 22 can be shifted to posterior at least by approximately half the thickness of the intraocular lens 11. With this preferred design, the greatest possible deformation and posterior displacement of the anterior optic element 22 is achieved. In FIG. 2j, the intraocular lenses as shown in FIGS. 2f and 2i are superimposed, so that the posterior oriented offset is visible, by which the anterior optic element 22 is shifted in far accommodation. The intra ocular lens in the near range is shown in continuous lines and the same in the far range is shown in dashed lines. This embodiment of intraocular lens 11 is particularly preferred with a biconvex optic element in the central area, which—as shown in FIG. 2j—is embodied as a 2-optic shift without filling, or as 1-optic shift where the latter is distinguished by a posterior pinhole.

In a plan view of an intraocular lens 11, FIG. 2h shows the shape of the haptic segments 24 as they are preferably used in intraocular lenses 11 with an overhang. This haptic segment differs from the embodiment shown in FIG. 2e, in that the leg is not linear in shape.

FIG. 2g also shows an embodiment of a capsular intraocular lens 11 with a filling which does not completely fill the cavity 29 and which is bounded by a membrane 291. The membrane 291 is stretched between the anterior and the posterior optic element 22, 21, so that the cavity 29, in which the filling is disposed, is delimited by the optic element 22, 21 and the membrane 291. In the detailed view of FIG. 2g, the connection between the membrane 291 and the optic element 21 and/or haptic element 23 is shown.

Alternatively, the filling can lie within a (not shown) full bag.

A capsular intraocular lens with an overhang may be injected, in another direction—thus rotated by 180°—into the capsular bag and is still accommodative, although in this case the implant is not anatomically adapted perfectly to the capsular bag.

Figure 3A:
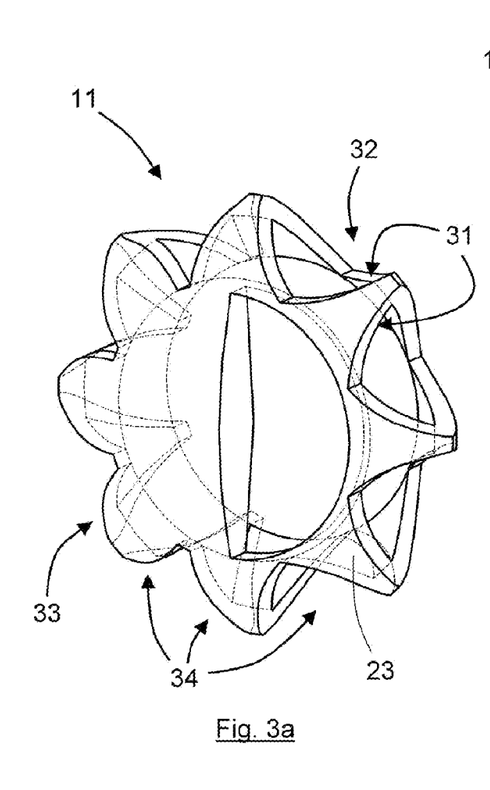
Figure 3B:
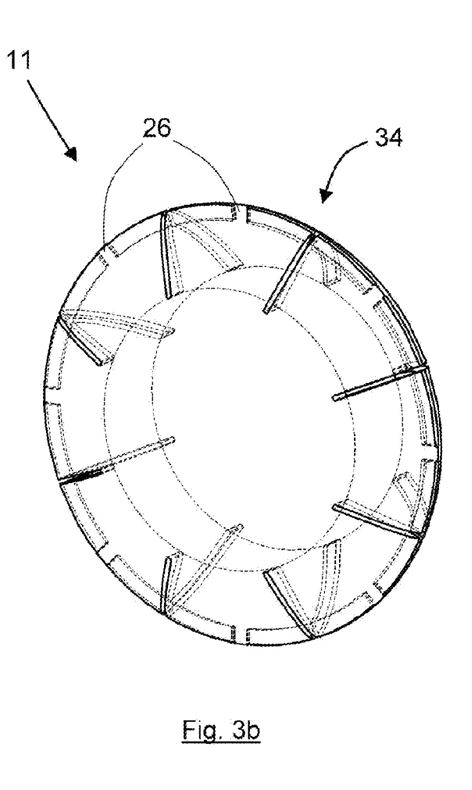
Figure 3C:
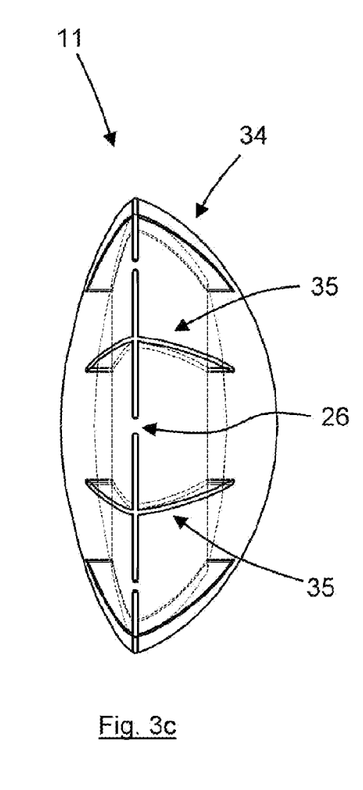

FIGS. 3a, b, and c illustrate alternative embodiments of an intraocular lens 11. In addition to the triangular haptic elements 24 provided in a plan view, also embodiments are provided in which the legs 31 of haptic elements 24 are concave (arrow 32) or convex (arrow 33) in form. Furthermore, also intraocular lenses 11 are provided in which the haptic elements 24 are formed by radial and circumferential cuts. FIGS. 3b and c show such a slit intraocular lens 34. In this embodiment the half-shells are interconnected by the webs 26, which are formed in that the cuts are aligned circumferentially not continuously over the entire equator of the intraocular lens. In a side view (FIG. 3c) cross-shaped slits (arrow 35) are provided, which extend along the equator up to the webs 26.

Figure 4A:
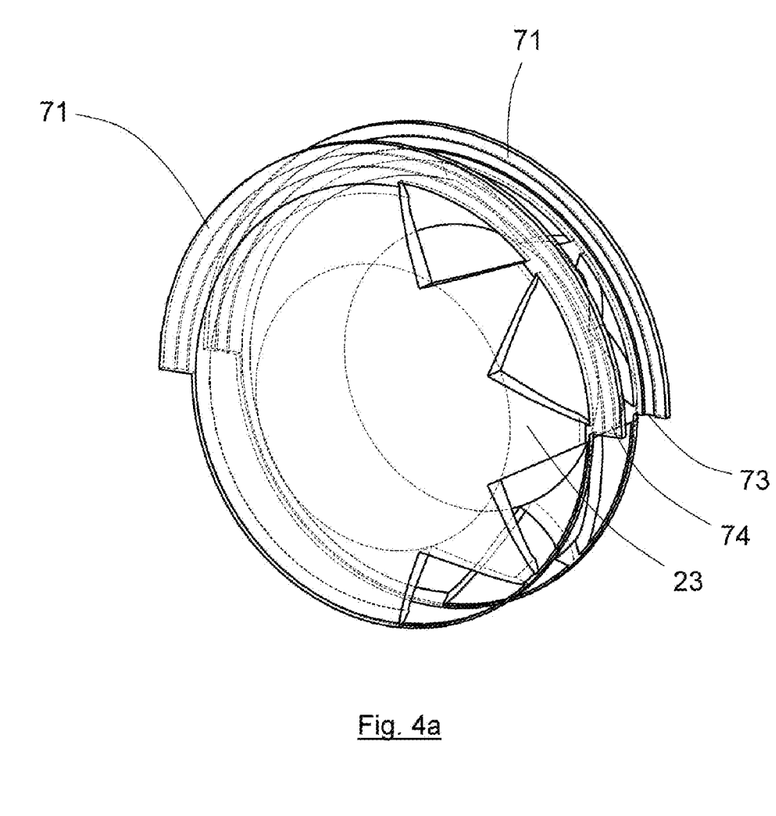
Figure 4B:
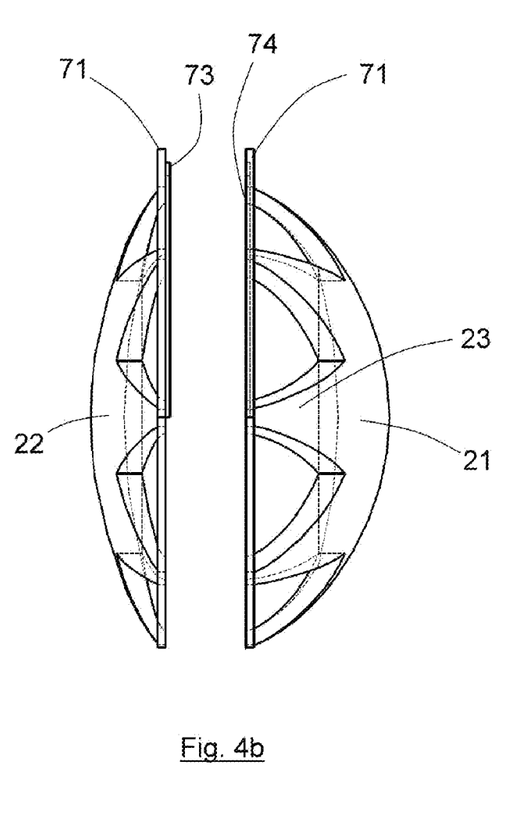

FIGS. 4a and b show concrete embodiments of intraocular lens half-shells with optic elements 21, 22 and haptic elements 23. On these half-shells, an annular portion 71 is formed in each case, so that it forms a kind of brim. The annular portion 71 forms a large contact surface, so that the shells can be easily assembled, whereby rotationally offset—feather and groove-shaped contours 73, 74 may be formed for better positioning and angular aligning.

Figure 5A:
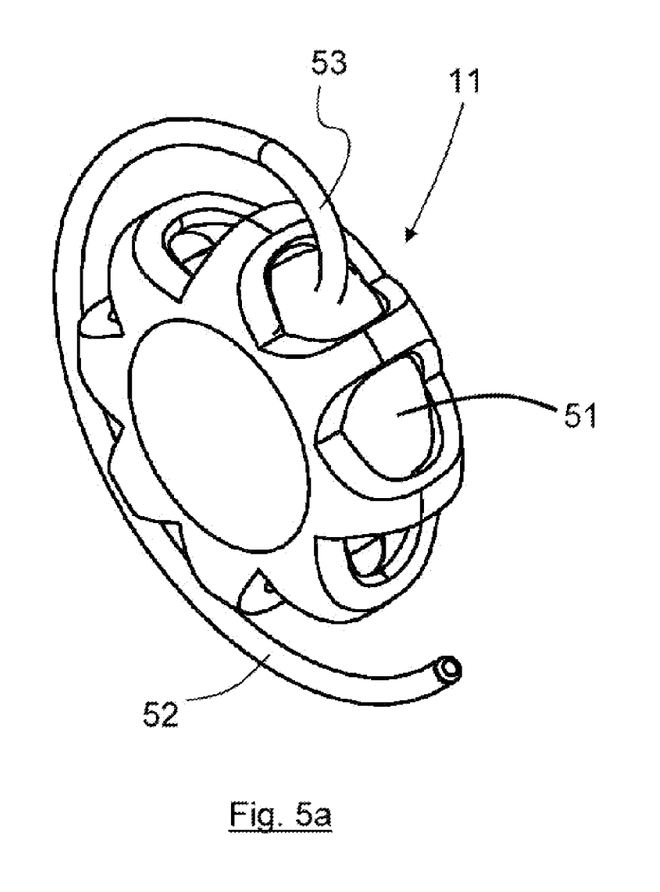
Figure 5B:
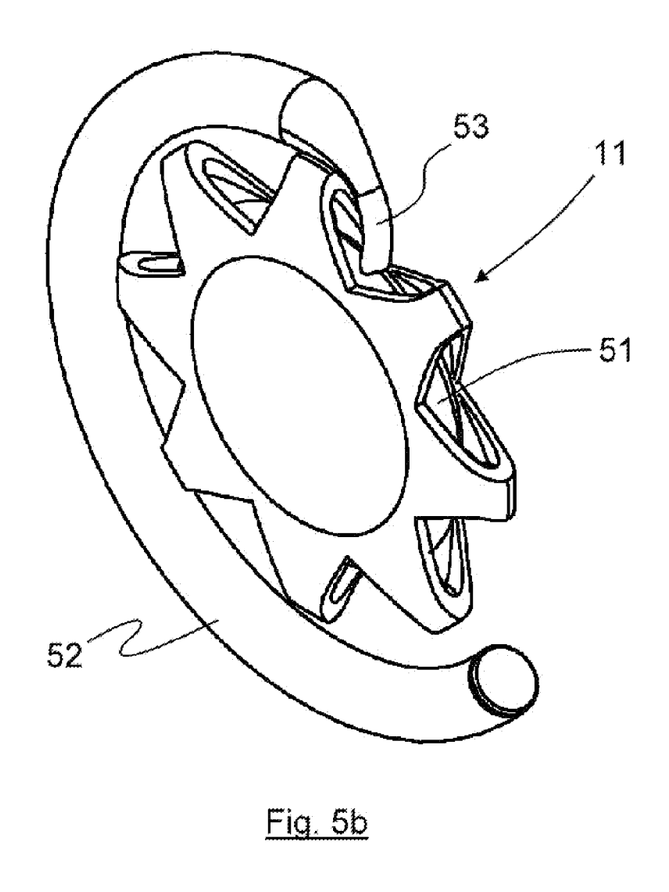

FIGS. 5a and 5b show a concrete embodiment of the present invention in which the cavity is formed, which in the illustrated embodiment is formed as a bag 51, is detachably connected to a reservoir 52. The reservoir 52 is tubular and connected to the bag via a hose. FIG. 5b shows an intraocular lens 11, in which the filling is located entirely within the reservoir 52, so that the intraocular lens 11 can be compressed flat. After implantation, the filling is fed from the reservoir 52 into the cavity, whereby the volume of the reservoir 52 is reduced and the volume of the cavity increased (cf. FIG. 5a). In this state, the reservoir 52 can be disconnected from the cavity by the above-described mechanisms. Due to simpler fabrication, the tubular reservoir as shown in FIG. 5a preferably has a uniform diameter. Here, however, the portion of the hose close to the intraocular lens has a greater wall thickness than the rest of the tube, so that only the part of the tube with the smaller wall thickness for receiving the filling inflates. In a short transition section, different wall thickness equalise. Of course, the tubular reservoir can also have different diameters along its length.

Figure 6:
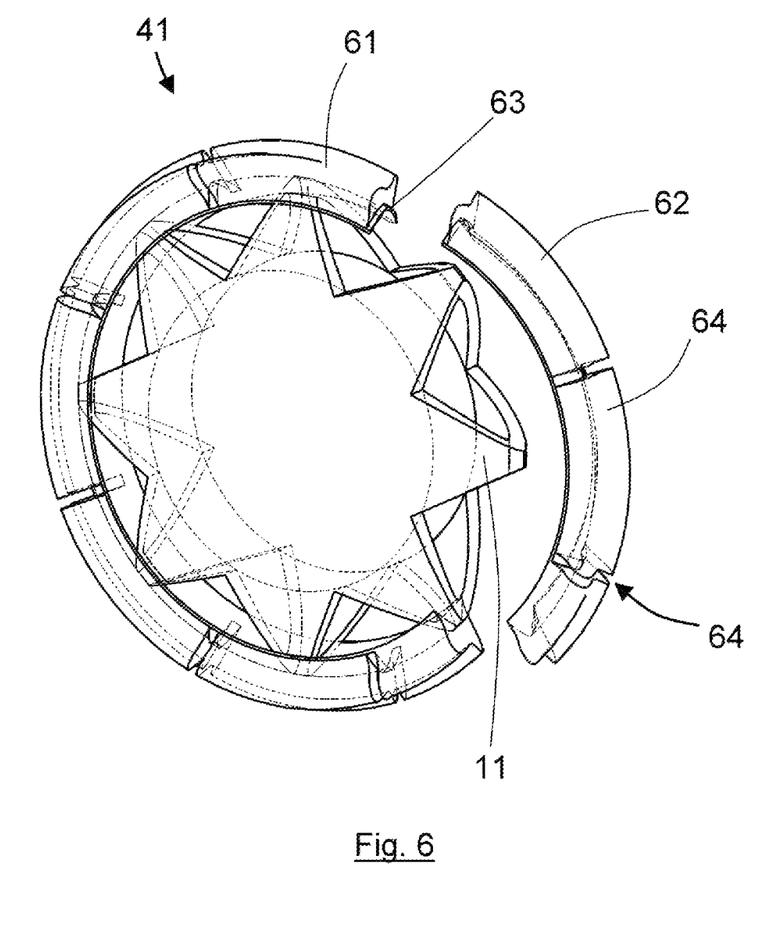

Unlike capsular intraocular lenses, ciliary intraocular lenses are in direct contact with the ciliary muscle, so that the force of contraction is transmitted directly to the ciliary intraocular lens. Here, in order to achieve a uniform deformation of the optic element or elements, the largest possible contact surface of the ciliary muscle is formed on the haptic elements, so that a haptic ring forms. FIG. 6 shows an embodiment in which the ciliary intraocular lenses 41 are divided by the haptic ring 61 to make them easier to introduce into the eye. Thus, the ciliary intraocular lens 41 is composed of a comparatively small intraocular lens 11 and a separate haptic ring 61. The separate haptic ring 61 is divided by recesses or apertures 64 in a plurality of segments 62, which are connected to each other with 63 membranes. The internal intraocular lens 11 may also be designed differently, whereby the described embodiments are preferred.

Explanation

The work that led to this invention was funded in accordance with the grant agreement No. CP-IP 214491-2 COTECH under the Seventh Framework Programme of the European Union ([FP7/2007-2013] [FP7/2007-2011]).

The invention claimed is:

1. An intraocular lens, in particular capsular intraocular lens, with at least an anterior optic and a posterior optic and a haptic connecting both optics, wherein a cavity is formed by the optics and haptic, which is opened by circumferentially arranged openings;
   wherein
   the haptic has an anterior and a posterior haptic segment that are connected to each other at the equator, wherein the anterior and the posterior haptic segments have a plurality of haptic elements, wherein the basis of two adjacent haptic elements abut each other or they have cumulative distances of 5% or 10% of the circumference corresponding to the radius of the bases, and wherein the section of the cavity between the optics has a filling, which is at least enclosed in part by a membrane, which
   a) is formed as a bag and completely encloses the filling,
   b) is ring-shaped and is connected with the anterior and posterior optic or
   c) closes the openings.

2. The intraocular lens according to claim 1 wherein the area of the cavity that is delimited by the haptic and/or the openings, is occupied partially or completely by the filling.

3. The intraocular lens according to claim 1 wherein the filling is liquid, gel-like, or gaseous and preferably comprises nano-particles.

4. The intraocular lens according to claim 1 wherein the filling has a higher refractive index than the aqueous humour.

5. The intraocular lens according to claim 1 wherein the membrane is water permeable.

6. The intraocular lens according to claim 1, wherein the haptic elements are substantially configured in triangular shape, wherein the bases of the triangular haptic elements transform substantially flush in the respective optic.

7. The intraocular lens according to claim 6 wherein the cumulative width of the tips of the haptic elements is less than 40% of the equatorial circumference.

8. The intraocular lens according to claim 1 wherein the anterior haptic segment at the transition to the anterior optic forms an overhang, wherein the anterior surface of the anterior haptic segment protrudes anterior over the edge of the anterior optic.

9. The intraocular lens according to claim 1 wherein the posterior surface of the anterior haptic segment, protrudes posterior beyond the posterior surface of the anterior optic.

10. The intraocular lens according to claim 1 wherein the anterior optic in the edge area is at least as thick or thicker than at the central optic axis and preferably has a convex outer surface.

11. The intraocular lens according to claim 1 wherein the anterior surface of the posterior haptic segment anterior protrudes beyond the anterior surface of the posterior optic.

12. The intraocular lens according to claim 1 wherein the posterior surface of the posterior haptic segment protrudes beyond the posterior surface of the posterior optic.

13. The intraocular lens according to claim 1, wherein by a cavity detachably connected to the reservoir, so that the filling of the reservoir is directed into the cavity.

14. The intraocular lens according to claim 13 wherein the reservoir is tubular and is preferably connected with the cavity via a micro-valve or a hollow needle or cannula.

15. The intraocular lens according to claim 13 wherein the reservoir is connected with the cavity via a hose, which is separable by melting.

16. The intraocular lens according to claim 13, wherein the connection point is disposed between the reservoir and the cavity on the membrane the haptic or outside the optic area of the optic.

17. The intraocular lens according to claim 1, wherein the thickness of the anterior haptic segment in its transverse section to the optic axis is at least as thick as the thickness of the anterior optic element at its edge or the thickness of the posterior haptic segment in the transverse section to the optic axis is at least as thick as the thickness of the posterior optic element at its edge.

18. An intraocular lens, in particular capsular intraocular lens, with at least an anterior optic and a posterior optic and a haptic connecting both optics, wherein a cavity is formed by the optics and haptic, which is opened by circumferentially arranged openings, wherein:
    the haptic has an anterior and a posterior haptic segment that are connected to each other at the equator, wherein the anterior and the posterior haptic segments have a plurality of haptic elements, wherein the basis of two adjacent haptic elements abut each other and wherein the section of the cavity between the optics has a filling, which is at least enclosed in part by a membrane, which
    a) is formed as a bag and completely encloses the filling, or
    b) closes the openings.

\* \* \* \* \*